US012389101B2

(12) United States Patent
Maeda et al.

(10) Patent No.: US 12,389,101 B2
(45) Date of Patent: Aug. 12, 2025

(54) IMAGE PICKUP UNIT AND ENDOSCOPE

(71) Applicant: OLYMPUS MEDICAL SYSTEMS CORP., Tokyo (JP)

(72) Inventors: Kazuya Maeda, Nagano (JP); Yukiharu Makino, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 29 days.

(21) Appl. No.: 18/220,462

(22) Filed: Jul. 11, 2023

(65) Prior Publication Data

US 2023/0353853 A1 Nov. 2, 2023

Related U.S. Application Data

(63) Continuation of application No. PCT/JP2021/017419, filed on May 6, 2021.

(51) Int. Cl.
*H04N 23/50* (2023.01)
*H04N 23/68* (2023.01)

(52) U.S. Cl.
CPC ....... *H04N 23/555* (2023.01); *H04N 23/6811* (2023.01)

(58) Field of Classification Search
CPC .. H04N 23/555; H04N 23/6811; H04N 23/54; A61B 1/04
USPC .......................................................... 348/65
See application file for complete search history.

(56) References Cited

U.S. PATENT DOCUMENTS 6,547,721 B1 4/2003 Higuma et al.
10,511,774 B2 * 12/2019 Takeuchi .............. H04N 5/145
2004/0176661 A1 9/2004 Futatsugi
2009/0078873 A1 3/2009 Sakemoto et al.
2017/0255001 A1 * 9/2017 Yamashita ............. A61B 1/051
2019/0038117 A1 * 2/2019 Motohara ................ A61B 1/04
2020/0333581 A1 * 10/2020 Kobayashi ......... G02B 23/2423

FOREIGN PATENT DOCUMENTS

EP 0 978 251 A1 2/2000
EP 1 455 216 A1 9/2004
JP 2000-115594 A 4/2000
JP 2000-225089 A 8/2000
JP 2002-159438 A 6/2002
JP 2004-267351 A 9/2004
JP 3955458 B2 8/2007
JP 2010-016733 A 1/2010
JP 6574448 B2 9/2019
WO 2017/195605 A1 11/2017
WO WO-2020218335 A1 * 10/2020 ......... H01L 21/4853

OTHER PUBLICATIONS

International Search Report dated Jul. 13, 2021 received in PCT/JP2021/017419.

* cited by examiner

*Primary Examiner* — William C Vaughn, Jr.
*Assistant Examiner* — Asteways Gettu Zewede
(74) *Attorney, Agent, or Firm* — Scully, Scott, Murphy & Presser, P.C.

(57) ABSTRACT

An image pickup unit includes an image sensor, a first circuit board on which a first land is disposed around four first side surfaces, a second circuit board on which a second land is disposed around four second side surfaces, a movement detection sensor housed in a recess of the first circuit board, and a rectangular tube bonded to the first land and the second land and sealing the recess in an airtight manner.

20 Claims, 6 Drawing Sheets

1 II 30 33 32 31 10 40 20 76 60 II O 20SB 30SA 30SB R10

1
30
38
75
30SB
30SA
O
10
15
10SS1
10SS2
10SS3
10SS4
18
71
R10
51
10SB
10SA
72A
40
72B
50
57
74
20
25
20SA
20SS1
20SS2
20SS3
20SS4
20SB
20SSL
60

IMAGE PICKUP UNIT AND ENDOSCOPE

CROSS REFERENCE TO RELATED APPLICATION

This application is a continuation application of PCT/JP2021/017419 filed on May 6, 2021, the entire contents of which are incorporated herein by this reference.

BACKGROUND OF THE INVENTION

1. Field of the Invention

The present invention relates to an image pickup unit in which an electronic component is disposed in a recess of a circuit board, and an endoscope including an image pickup unit in which an electronic component is disposed in a recess of a circuit board.

2. Description of the Related Art

An endoscope is widely used in medical and industrial fields. An endoscope in which an electronic component other than an image pickup device is disposed at a distal end portion of an insertion portion to add a new function to the endoscope and increase performance has been developed.

Japanese Patent No. 657448 discloses an endoscope configured to control focusing by detecting a relative moving amount with respect to an object by using a motion sensor disposed at a distal end portion of an insertion portion. The sensor is connected to a sensor cable for transmitting and receiving signals.

SUMMARY OF THE INVENTION

An image pickup unit of an embodiment includes: an image sensor including a front surface and a back surface on which a back surface electrode is disposed; a first circuit board including a first principal surface on which a first electrode is disposed, a second principal surface on which a second electrode is disposed, and four first side surfaces, a first land being disposed around the four first side surfaces, the first electrode being bonded to the back surface electrode; a second circuit board including a third principal surface on which a third electrode is disposed, a fourth principal surface, and four second side surfaces, a second land being disposed around the four second side surfaces, the third electrode being bonded to the second electrode; an electronic component housed in a recess, at least one of the second principal surface or the third principal surface including the recess; and a rectangular tube bonded to the first land and the second land and sealing the recess in an airtight manner.

An endoscope of an embodiment includes an image pickup unit, and the image pickup unit includes; an image sensor including a front surface and a back surface on which a back surface electrode is disposed; a first circuit board including a first principal surface on which a first electrode is disposed, a second principal surface on which a second electrode is disposed, and four first side surfaces, a first land being disposed around the four first side surfaces, the first electrode being bonded to the back surface electrode; a second circuit board including a third principal surface on which a third electrode is disposed, a fourth principal surface, and four second side surfaces, a second land being disposed around the four second side surfaces, the third electrode being bonded to the second electrode; an electronic component housed in a recess, at least one of the second principal surface or the third principal surface including the recess; and a rectangular tube bonded to the first land and the second land and sealing the recess in an airtight manner.

DETAILED DESCRIPTION OF THE PREFERRED EMBODIMENTS

First Embodiment

Figure 1:
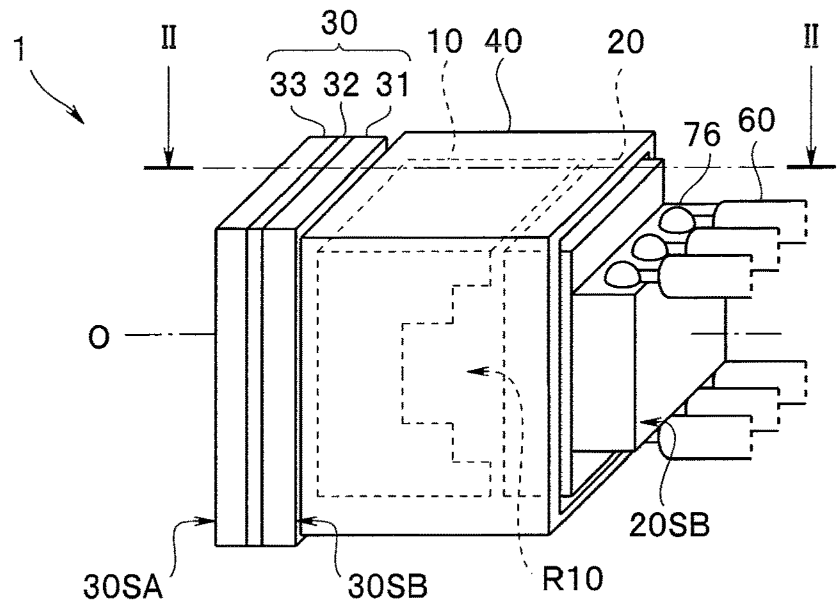
FIG. 1 is a perspective view of an image pickup unit according to a first embodiment.
Figure 2:
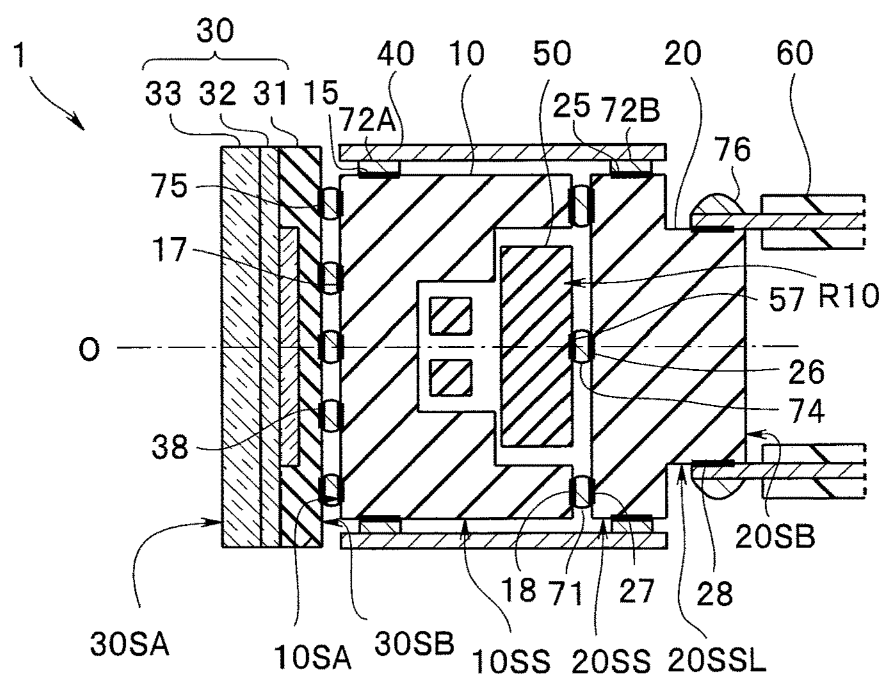
FIG. 2 is a cross-sectional view taken along line 11-11 in FIG. 1.
Figure 3:
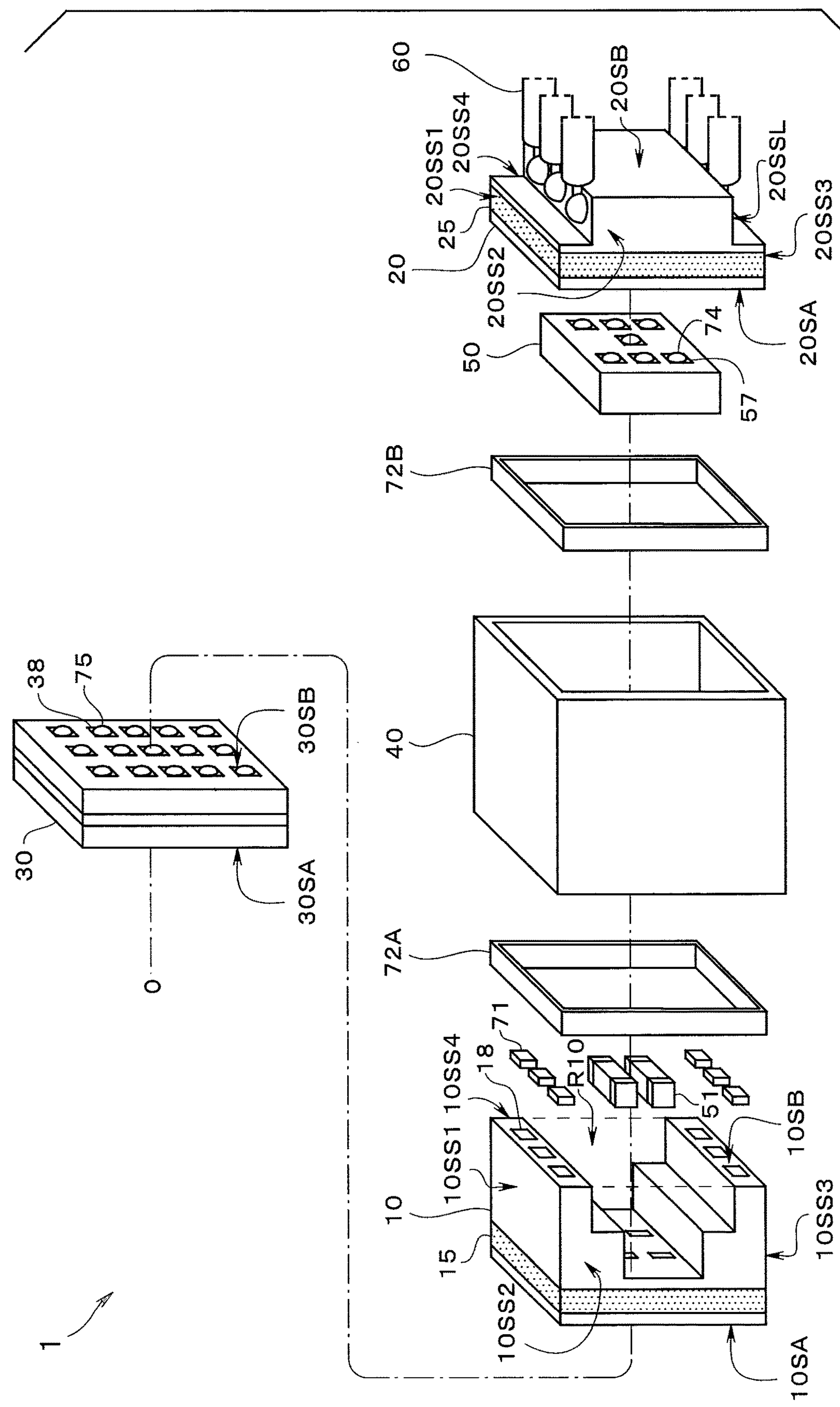
FIG. 3 is a perspective exploded view of the image pickup unit according to the first embodiment.

An image pickup unit 1 according to the present embodiment illustrated in FIGS. 1, 2, and 3 includes a first ceramic circuit board 10, a second ceramic circuit board 20, an image sensor 30, a rectangular tube 40, a movement detection sensor 50 as an electronic component, and a cable 60.

Note that diagrams based on embodiments are schematic. A relation between thickness and width of each part, a thickness ratio of each part, and the like are different from those in reality. A dimensional relation and a ratio are different between parts of drawings. Illustration and reference sign provision of some constituent components are omitted. A side on which light is incident is referred to as "front".

The first ceramic circuit board 10 (hereinafter referred to as "first circuit board 10") and the second ceramic circuit board 20 (hereinafter referred to as "second circuit board 20") are stereoscopic circuit boards in which a plurality of ceramic wiring layers are stacked. Each ceramic circuit board is produced by stacking and baking a plurality of unbaked ceramic sheets each having surface wiring and through wiring.

The first circuit board 10 has a first principal surface 10SA, a second principal surface 10SB opposite the first principal surface 10SA, and four first side surfaces 10SS1 to 10SS4. Hereinafter, each of the four first side surfaces 10SS1 to 10SS4 is referred to as a first side surface 10SS. A principal surface is a surface orthogonal to an optical axis O, and a side surface is a surface parallel to the optical axis O.

A plurality of first electrodes 17 are disposed on the first principal surface 10SA. A plurality of second electrodes 18 are disposed on the second principal surface 10SB.

The second principal surface 10SB has a recess R10. The recess R10 is a groove reaching the two first side surfaces 10SS2 and 10SS4. The recess R10 may be a bottomed hole. An electronic component 51 such as a chip capacitor is mounted on a bottom surface of the recess R10. A first land 15 is disposed on the first circuit board 10 around the four first side surfaces 10SS1 to 10SS4 without discontinuity. Note that corners at which the four first side surfaces 10SS1 to 10SS4 intersect each other may be chamfered. Lands and electrodes made of a sintered electric conductor have high solder wettability.

The second circuit board 20 includes a third principal surface 20SA, a fourth principal surface 20SB opposite the third principal surface 20SA, and four second side surfaces 20SS1 to 20SS4. Hereinafter, each of the four second side surfaces 20SS1 to 20SS4 is referred to as a second side surface 20SS.

A plurality of third electrodes 27 and a plurality of fourth electrodes 26 are disposed on the third principal surface 20SA. The second circuit board 20 has a land side surface 20SSL parallel to the second side surface 20SS1 at a back part. A plurality of cable lands 28 are disposed on the land side surface 20SSL. The cables 60 for the image sensor 30 or the movement detection sensor 50 to transmit and receive electric signals are bonded to the cable lands 28 by solder 76. A second land 25 is disposed on the second circuit board 20 around the four second side surfaces 20SS1 to 20SS4 without discontinuity.

Electrodes 57 of the movement detection sensor 50 as an electronic component are bonded to the plurality of fourth electrodes 26 by fourth solder 74. The movement detection sensor 50 is, for example, a six-axis inertial measurement unit (IMU) constituted by a three-axis acceleration sensor and a three-axis gyro sensor. The acceleration sensor measures acceleration, and the gyro sensor measures angular velocity. The IMU is manufactured by an MEMS technology of simultaneously and collectively manufacturing, on a silicon wafer, a large number of components including a movable member such as a cantilever and a piezoelectric element or the like configured to detect change of the movable member. The movement detection sensor 50 may be, for example, the acceleration sensor or the gyro sensor.

The second electrodes 18 on the second principal surface 10SB of the first circuit board 10 are bonded to the third electrodes 27 on the third principal surface 20SA of the second circuit board 20 by first solder 71. When the first circuit board 10 and the second circuit board 20 are bonded to each other, a front part of the movement detection sensor 50 is disposed in the recess R10 of the first circuit board 10. Note that each first side surface 10SS of the first circuit board 10 and the corresponding second side surface 20SS of the second circuit board 20 are positioned on the same plane. In other words, when projected onto a virtual surface orthogonal to the optical axis O, a first projection image of the first principal surface 10SA and a third projection image of the third principal surface 20SA overlap each other.

The image sensor 30 has a front surface 30SA and a back surface 30SB opposite the front surface 30SA. A plurality of back surface electrodes 38 are disposed on the back surface 30SB. The image sensor 30 includes an image pickup device 31, a cover glass 33, and a transparent resin layer 32 bonding the cover glass 33 to the image pickup device 31. The back surface electrodes 38 connected to the image pickup device 31 via through wiring (not illustrated) are bonded to the first electrodes 17 of the first circuit board 10 by fifth solder 75. The image pickup device 31 is, for example, a CCD element or a CMOS image pickup element. The image pickup device 31 may be a front-illuminated image sensor or a back-illuminated image sensor.

One or more semiconductor elements configured to process image pickup signals may be stacked on a back surface of the image pickup device 31, and the back surface electrodes 38 may be disposed on a back surface of each semiconductor element, which is the back surface 30SB of the image sensor 30.

Figure 5A:
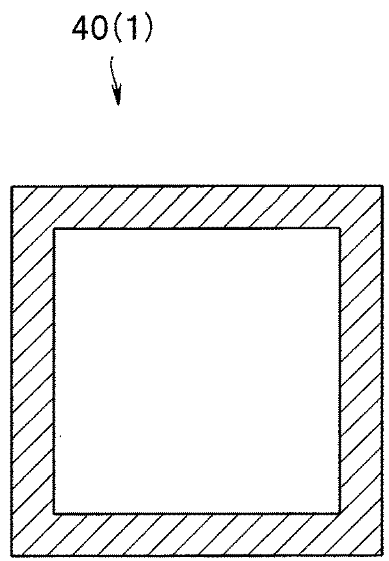
FIG. 5A is a cross-sectional view of a rectangular tube of the image pickup unit according to the first embodiment.

The rectangular tube 40 having a substantially rectangular cylindrical outer shape is a metal plate sealing the recess R10 in an airtight manner. For example, the rectangular tube 40 is made of copper having a thickness of 50 μm to 100 μm. As illustrated in FIG. 5A, a hollow of the rectangular tube 40 has a rectangular section orthogonal to the optical axis O. Comparison of projection images projected onto a virtual surface orthogonal to the optical axis O indicates that the hollow has a projection image slightly larger than the first projection image of the first principal surface 10SA and the third projection image of the third principal surface 20SA.

A length (dimension in a direction parallel to the optical axis O) of the rectangular tube 40 is longer than a distance between the first land 15 of the first circuit board 10 and the second land 25 of the second circuit board 20. Thus, the first land 15 and the second land 25 are covered by the rectangular tube 40. Corners of inner and outer surfaces of the rectangular tube 40 may be chamfered.

The inner surface of the rectangular tube 40 and the first land 15 are bonded to each other without a gap by second solder 72A, and the inner surface of the rectangular tube 40 and the second land 25 are bonded to each other without a gap by second solder 72B. Hereinafter, each of the second solders 72A and 72B is referred to as a second solder 72.

The recess R10 is sealed in an airtight manner by the rectangular tube 40. Specifically, the first circuit board 10, the second circuit board 20, the rectangular tube 40, and the second solders 72A and 72B form an airtight-sealing (hermetic seal) structure that blocks the recess R10 from external air.

A distal end portion of an insertion portion is affected by humidity and external air in sterilization processing as well as in use and storage. Thus, characteristics of an electronic component, which is likely to be affected by humidity and external air, potentially change and reliability of an endoscope degrades. Furthermore, in an endoscope including an electronic component at a distal end portion of an insertion portion, a cable for the electronic component needs to be disposed at the distal end portion having a small diameter, and thus manufacturing of the endoscope is complicated.

The image pickup unit 1 includes the movement detection sensor 50 and thus has high performance. Ceramic and metal have extremely small moisture permeability and gas permeability. The movement detection sensor 50 is sealed by resin and thus swells due to influence of humidity or the like, and accordingly, the movable member inside is pressed, which potentially causes error to output values. However, since airtight sealing is provided by ceramic (the first circuit board 10 and the second circuit board 20) and metal (the rectangular tube 40 and the second solders 72A and 72B), the influence of humidity or the like is reduced and occurrence of error in output values is reduced, and thus the image pickup unit 1 has high reliability. Moreover, since the rectangular tube 40 is a thin metal plate, a dimension of the image pickup unit 1 in a direction orthogonal to the optical axis does not increase when the image pickup unit 1 is provided with an airtight sealing function.

In the image pickup unit 1, the movement detection sensor 50 is integrated with the image sensor 30 and transmits and receives signals through the cables 60 bonded to the second circuit board 20, and thus can be easily manufactured.

The rectangular tube 40 is made of metal with high thermal conductivity and thus has a high heat-releasing effect. Note that a front part of the rectangular tube 40 may contact the image sensor 30 to efficiently release heat generated by the image sensor 30. Moreover, the rectangular tube 40 is made of an electric conductor and thus also has an electromagnetic noise shielding effect.

In a method of manufacturing the image pickup unit 1, the movement detection sensor 50 is bonded to the second circuit board 20 by the fourth solder 74. Then, the first circuit board 10 and the second circuit board 20 are bonded to each other by the first solder 71. Then, the rectangular tube 40 is bonded to the first land 15 and the second land 25 by the second solders 72A and 72B.

To prevent remelting of any bonded part already soldered, a melting point of the first solder 71 is preferably lower than a melting point of the fourth solder 74 and higher than a melting point of the second solders 72A and 72B. Note that the melting point of the first solder 71 is more preferably lower than the melting point of the fourth solder 74 and higher than the melting point of the second solders 72A and 72B.

For example, a metal film such as copper may be disposed by using a plating method on electrodes and lands made of a sintered electric conductor. A solder ball, solder paste, or the like for bonding does not need to be disposed on electrodes and lands on which a solder film made of Sn or the like is disposed. In the first circuit board in which the recess R10 is a bottomed hole, a width (dimension in the optical axis direction) of the first land 15 may be substantially equal to a width of each first side surface 10SS. Voids of the solder film can be reduced by increasing the width of the first land 15.

The electronic component sealed in the recess R10 is not limited to the movement detection sensor 50. However, effects of the present invention are particularly significant when the electronic component is a sensor that includes a movable member and is likely to be affected by extremal air. As in the image pickup unit 1, not only the movement detection sensor 50 but also the electronic component 51 for signal processing at the image pickup device 31 may be housed in the recess R10.

<Modifications of First Embodiment>

Image pickup units 1A to 1C3 according to Modifications 1 to 7 of the first embodiment are similar to the image pickup unit 1 and have the same effects, and thus any constituent component having the same function is denoted by the same reference sign and description of the constituent component is omitted.

<Modification 1 of First Embodiment>

Figure 4:
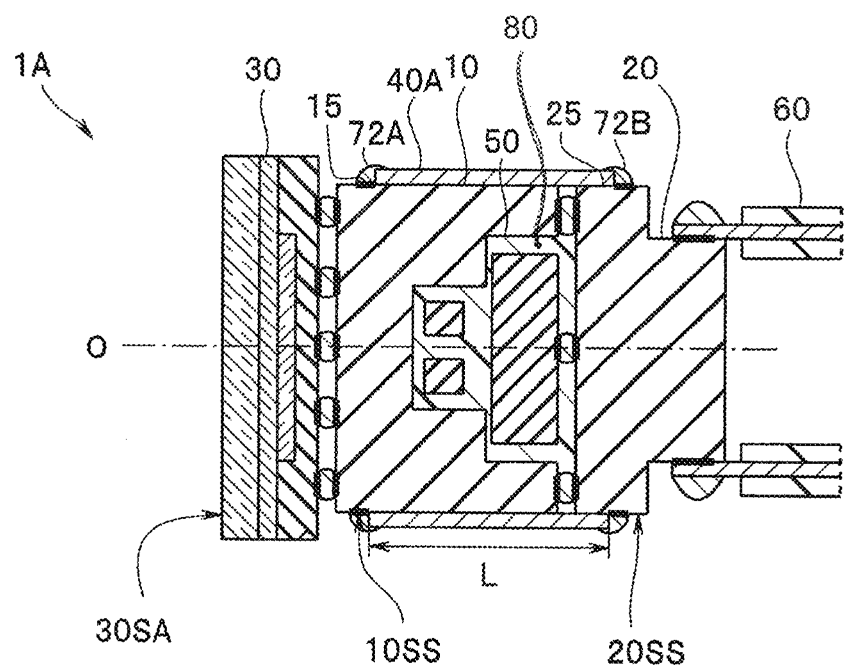
FIG. 4 is a cross-sectional view of an image pickup unit of Modification 1 of the first embodiment.

A rectangular tube 40A of the image pickup unit 1A according to the present modification illustrated in FIG. 4 has a length (dimension in the optical axis direction) L shorter than the rectangular tube 40 and substantially equal to an interval between the first land 15 and the second land 25.

Side surfaces of the rectangular tube 40A at both ends are bonded to the first land 15 and the second land 25 without a gap by the second solders 72A and 72B, respectively. Accordingly, the movement detection sensor 50 disposed in the recess R10 is sealed in an airtight manner.

Since an inner surface of the rectangular tube 40A contacts the first side surfaces 10SS and the second side surfaces 20SS, the image pickup unit 1A has a small outer dimension orthogonal to the optical axis O. Moreover, with the image pickup unit 1A, it is easy to observe disposition of the second solders 72A and 72B and whether the rectangular tube 40A is bonded without a gap by the second solders 72A and 72B.

In the image pickup unit 1A, the recess R10 is filled with sealing resin 80. The sealing resin 80 is, for example, epoxy resin, polyimide resin, benzocyclobutene (BCB) resin, or silicone resin.

Since the recess R10 is filled with the sealing resin 80, the movement detection sensor 50 is unlikely to be affected by external air and thus the image pickup unit 1A has higher reliability than the image pickup unit 1. The sealing resin 80 may fill a gap between the second principal surface 10SB and the third principal surface 20SA and a gap between the inner surface of the rectangular tube 40A and each of the first side surfaces 10SS and the second side surfaces 20SS. The image pickup unit 1 preferably includes the sealing resin 80 filling the recess R10 or the like.

<Modification 2 of First Embodiment>

Figure 5B:
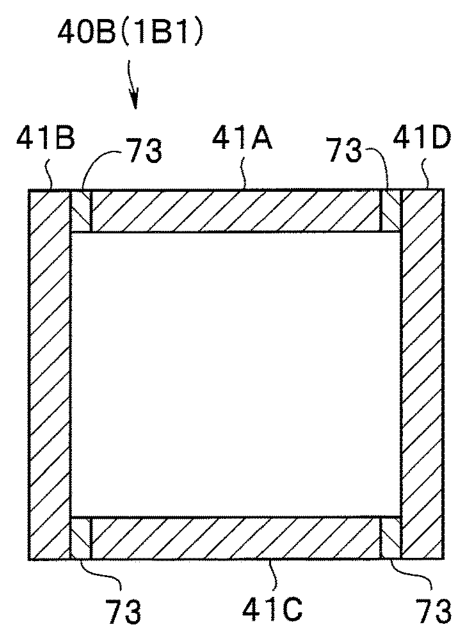
FIG. 5B is a cross-sectional view of a rectangular tube of an image pickup unit of Modification 2 of the first embodiment.

As illustrated in FIG. 5B, a rectangular tube 40B of the image pickup unit 1B1 according to the present modification includes four metal plates 41A, 41B, 41C, and 41D and third solder 73 bonding the metal plates 41A, 41B, 41C, and 41D.

A method of manufacturing the rectangular tube 40B will be briefly described below. The metal plate 41A is bonded to the first land 15 on the first side surface 10SS1 and the second land 25 on the second side surface 20SS1 by using the second solders 72A and 72B. The metal plate 41C is bonded to the first land 15 on the first side surface 10SS3 and the second land 25 on the second side surface 20SS3 by using the second solders 72A and 72B.

Thereafter, the metal plate 41B is bonded to the first land 15 on the first side surface 10SS2 and the second land 25 on the second side surface 20SS2 by using the second solders 72A and 72B. The metal plate 41D is bonded to the first land 15 on the first side surface 10SS4 and the second land 25 on the second side surface 20SS4 by using the second solders 72A and 72B. Then, the four metal plates 41A. 41B, 41C, and 41D are bonded to each other by using the third solder 73.

<Modification 3 of First Embodiment>

Figure 5C:
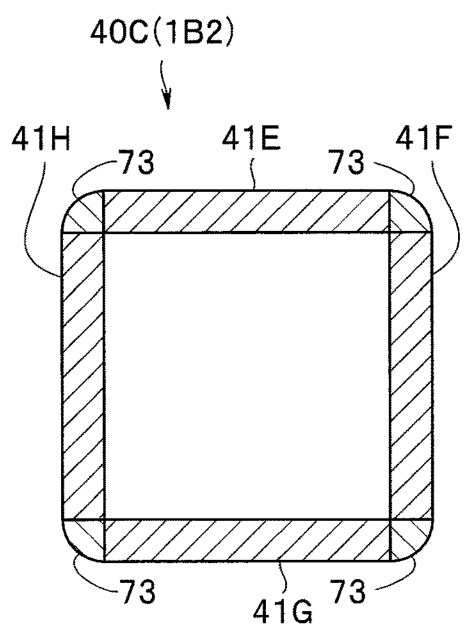
FIG. 5C is a cross-sectional view of a rectangular tube of an image pickup unit of Modification 3 of the first embodiment.
Figure 5D:
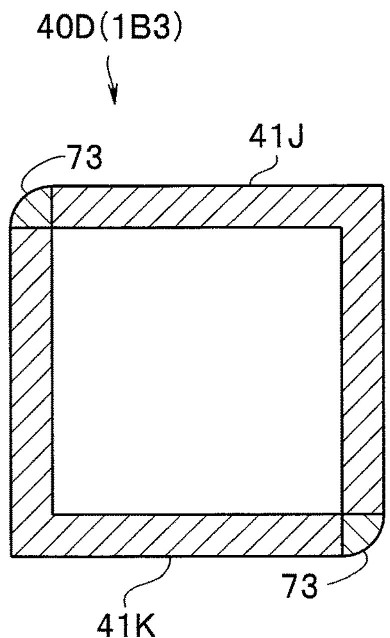
FIG. 5D is a cross-sectional view of a rectangular tube of an image pickup unit of Modification 4 of the first embodiment.

As illustrated in FIG. 5C, a rectangular tube 40C of the image pickup unit 1B2 according to the present modification includes four metal plates 41E, 41F, 41G, and 41H and the third solder 73 bonding the metal plates 41E, 41F, 41G, and 41H.

A method of manufacturing the rectangular tube 40C will be briefly described below. The metal plates 41E, 41F, 41G, and 41H are each bonded to the first land 15 of the first circuit board 10 and the second land 25 of the second circuit board 20 by using the second solders 72A and 72B. Then, the four metal plates 41E, 41F, 41G, and 41H are bonded to each other by using the third solder 73.

<Modification 4 of First Embodiment>

As illustrated in FIG. 5C, a rectangular tube 40D of the image pickup unit 1B3 according to the present modification includes two metal plates 41J and 41K having L-shaped sections orthogonal to the optical axis O, and the third solder 73 bonding the metal plates 41J and 41K.

A method of manufacturing the rectangular tube 40D will be briefly described below. The metal plate 41J is bonded to the first land 15 on the first side surfaces 10SS1 and 10SS4 and the second land 25 on the second side surfaces 20SS1 and 20SS4 by using the second solders 72A and 72B. The metal plate 41K is bonded to the first land 15 on the first side surfaces 10SS2 and 10SS3 and the second land 25 on the second side surfaces 20SS2 and 20SS3 by using the second solders 72A and 72B. Then, the two metal plates 41J and 41K are bonded to each other by using the third solder 73.

The image pickup units 1B1 to 1B3 including the rectangular tubes 40B to 40D in which a plurality of metal plates are bonded to each other without a gap by the third solder 73 can be more easily manufactured than the image pickup unit 1. Note that each metal plate is not limited to a flat plate made of copper but only needs to be any plate that can be bonded by soldering. Each metal plate may have a U-shaped section.

To prevent remelting of a bonded part already soldered, a melting point of each second solder 72 is preferably lower than the melting point of the first solder 71 and higher than a melting point of the third solder 73. Note that the melting point of each second solder 72 is more preferably lower than the melting point of the first solder 71 and higher than the melting point of the third solder 73.

<Modification 5 of First Embodiment>

Figure 6A:
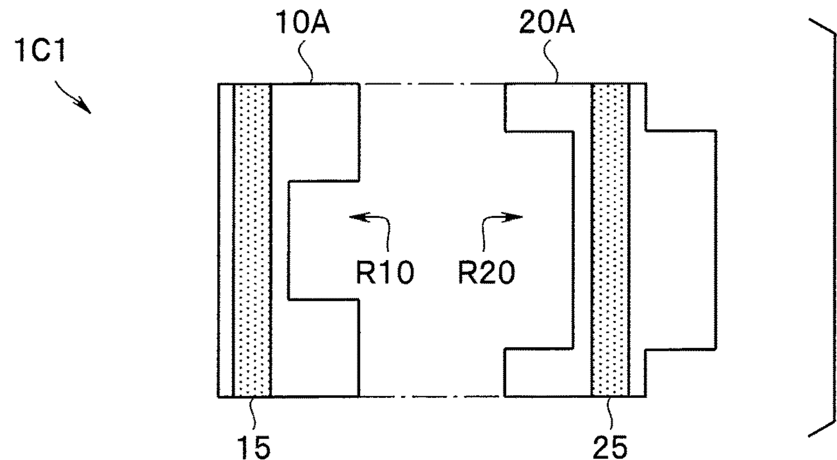
FIG. 6A is a side view of a circuit board of an image pickup unit of Modification 5 of the first embodiment.

In the image pickup unit 1C1 according to the present modification illustrated in FIG. 6A, a first circuit board 10A has the recess R10 and a second circuit board 20A has a recess R20.

<Modification 6 of First Embodiment>

Figure 6B:
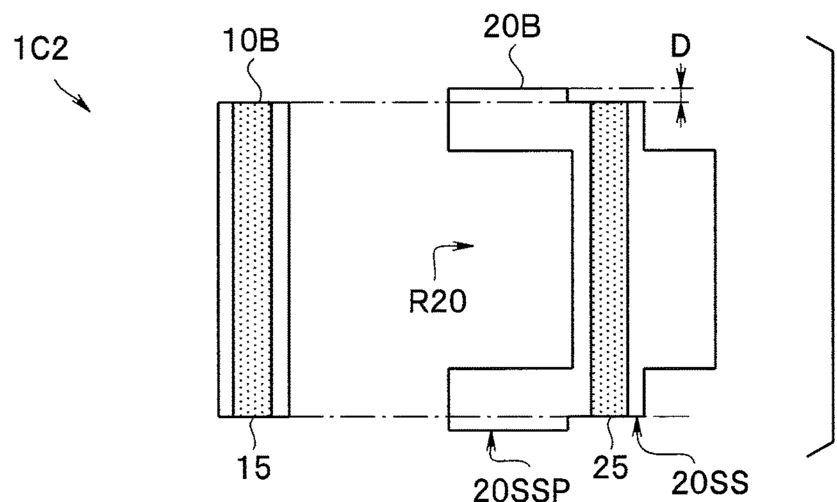
FIG. 6B is a side view of a circuit board of an image pickup unit of Modification 6 of the first embodiment.

In the image pickup unit 1C2 according to the present modification illustrated in FIG. 6B, a first circuit board 10B has no recess and a second circuit board 20B has the recess R20. Side surfaces 20SSP of the second circuit board 20B protrude by a step D as compared to the second side surfaces 20SS2 on which the second land 25 is disposed.

The step D is set to thicknesses of the second solders 72A and 72B. The first land 15 of the first circuit board 10B has the same dimensions as dimensions of the second land 25. Thus, although not illustrated, when the rectangular tube 40 is bonded to the first land 15 and the second land 25 by the second solders 72A and 72B, the inner surface of the rectangular tube 40 contacts the four side surfaces 20SSP, and accordingly, the image pickup unit 1C2 has a small outer dimension orthogonal to the optical axis.

<Modification 7 of First Embodiment>

Figure 6C:
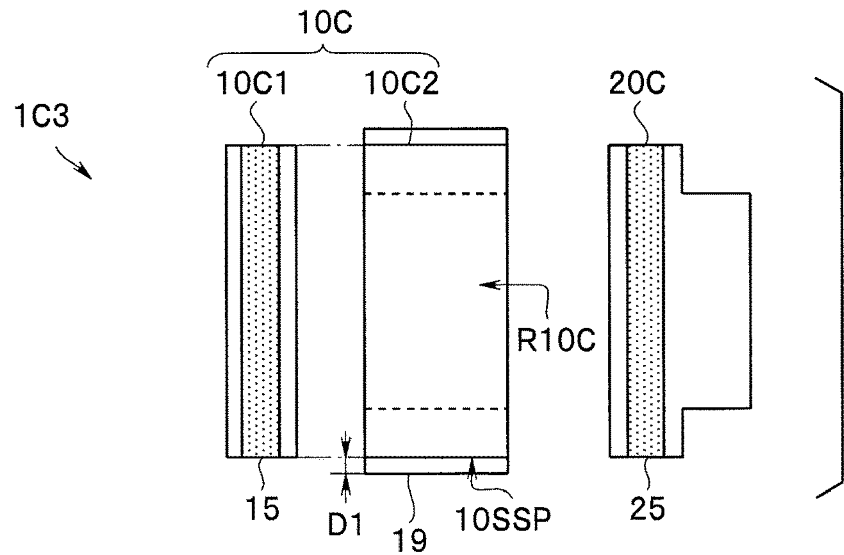
FIG. 6C is a side view of a circuit board of an image pickup unit of Modification 7 of the first embodiment.

In the image pickup unit 1C3 according to the present modification illustrated in FIG. 6C, a first circuit board 10C has a circuit board 10C1 bonded to a tubular circuit board 10C2. Specifically, a recess R10C is formed by the tubular circuit board 10C2. The tubular circuit board 10C2 may be bonded to a second circuit board 20C. The tubular circuit board may be bonded to each of the first circuit board and the second circuit board.

In the image pickup unit 1C3, a spacer member 19, such as a heat contraction tube, having a thickness D1 and surrounding an outer periphery of the tubular circuit board 10C2 is disposed on the tubular circuit board 10C2. The thickness D1 is set to the thicknesses of the second solders 72A and 72B. Since the inner surface of the rectangular tube contacts the spacer member 19, the image pickup unit 1C3 has a small outer dimension orthogonal to the optical axis.

As described for the image pickup units 1C1 to 1C3 according to Modifications 5 to 7, in each image pickup unit of the present invention, at least one of the second principal surface or the third principal surface needs to have a recess in which an electronic component is disposed and that is sealed in an airtight manner. The recess may be constituted by a tubular circuit board separated from the first circuit board and the second circuit board. Moreover, the inner surface of the rectangular tube 40 may contact the side surfaces of the circuit boards.

Note that each image pickup unit of the present invention may include two or more configurations of the image pickup units 1A to 1C3 according to Modifications 1 to 7. For example, the second circuit board of the image pickup unit 1A according to Modification 1 may have a recess as in the image pickup unit 1C1 according to Modification 5.

Second Embodiment

Figure 7:
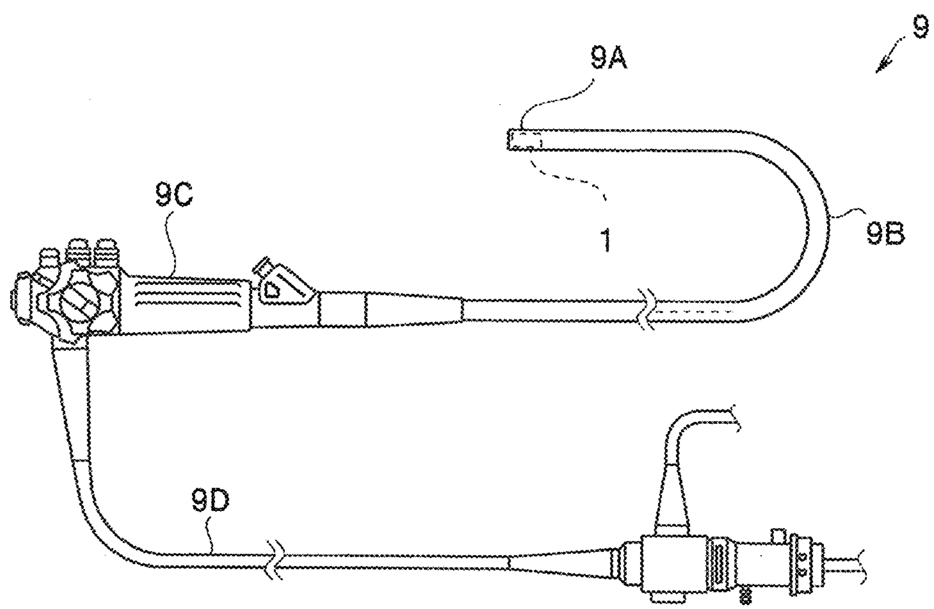
FIG. 7 is an exterior diagram of an endoscope according to a second embodiment.
Figure 8:
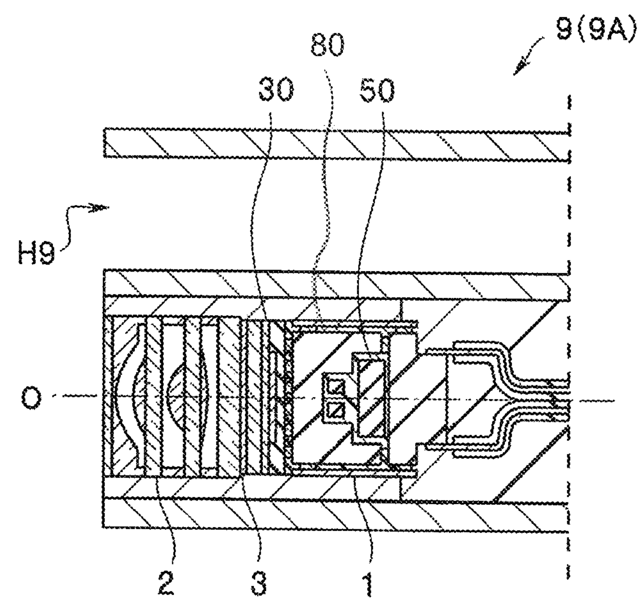
FIG. 8 is a cross-sectional view of a distal end portion of the endoscope according to the second embodiment.

An endoscope 9 according to the present embodiment illustrated in FIGS. 7 and 8 includes an insertion portion 9B in which the image pickup unit 1 is disposed at a distal end portion 9A, an operation portion 9C disposed on a proximal end side of the insertion portion 9B, and a universal code 9D extending from the operation portion 9C.

As illustrated in FIG. 8, a lens unit 2 in which a plurality of optical elements are stacked is bonded to the front surface 30SA of the image pickup unit 1 by using transparent resin 3. The image pickup unit 1 is inserted into a through-hole of the distal end portion 9A. A through-hole H9 as a treatment instrument channel is formed in the distal end portion 9A.

The lens unit 2 is, for example, a hybrid lens unit including a plano-concave lens, a convexo-plane lens, a convexo-convex lens, an infrared cut filter, a flare aperture, a brightness aperture, and the like. The lens unit 2 forms, on the image pickup device 31, an image of light incident from a front surface 2SA. The lens unit 2 has a configuration that is set as appropriate in accordance with specifications.

As described above, the image pickup unit 1 includes the movement detection sensor 50 and thus has high performance. The movement detection sensor 50 including a movable member is likely to be affected by humidity or the like but is sealed in an airtight manner by ceramic (the first circuit board 10 and the second circuit board 20) and metal (the rectangular tube 40 and the second solders 72A and 72B). Moreover, the dimension of the image pickup unit 1 in the direction orthogonal to the optical axis does not increase when the image pickup unit 1 is provided with an airtight sealing function.

The endoscope 9 includes the image pickup unit 1 and thus has high performance and high reliability and includes a small-diameter distal end portion. Moreover, the image pickup unit 1 can be easily manufactured since the movement detection sensor 50 is integrated with the image sensor 30.

It should be clear that an endoscope including any of the image pickup units 1A to 1C3 according to Modifications 1 to 6 at the distal end portion has effects of the endoscope 9 including the image pickup unit 1 as well as the effects of the relevant image pickup unit.

The endoscope may be a flexible endoscope including a flexible insertion portion or may be a rigid endoscope including a rigid insertion portion. The endoscope may be used in medical and industrial fields.

The present invention is not limited to the above-described embodiments and modifications but may be changed and modified in various kinds of manners without changing the scope of the invention.

What is claimed is:

1. An image pickup unit comprising:

an image sensor including a back surface on which a back surface electrode is disposed;

a first circuit board including:

a first principal surface on which a first electrode is disposed, the first electrode being bonded to the back surface electrode;

a second principal surface on which a second electrode is disposed, and a first side surface;

a second circuit board including:

a third principal surface on which a third electrode is disposed, the third electrode being bonded to the second electrode; and a second side surface;

an electronic component housed in a recess, at least one of the second principal surface or the third principal surface including the recess; and a tube bonded to each of the first land and the second land to seal the recess in an airtight manner.

2. The image pickup unit according to claim 1, wherein the electronic component is a movement detection sensor.

3. The image pickup unit according to claim 1, wherein the first circuit board includes a first land disposed on the first side surface, the second circuit board includes a second land disposed on the second side surface, the second and the third electrodes are bonded to each other by first solder, and each of the first and the second lands are bonded to the tube by second solder.

4. The image pickup unit according to claim 3, wherein the tube is a rectangular tube comprising a plurality of plates and third solder bonding the plurality of plates.

5. The image pickup unit according to claim 4, wherein a melting point of the second solder is lower than a melting point of the first solder and higher than a melting point of the third solder.

6. The image pickup unit according to claim 1, further comprising sealing resin filling the recess.

7. The image pickup unit according to claim 6, wherein the sealing resin fills a gap between an inner surface of the tube and each of the first and the second side surfaces.

8. An endoscope comprising:

an image pickup unit comprising:

an image sensor including a back surface on which a back surface electrode is disposed;

a first circuit board including:

a first principal surface on which a first electrode is disposed, the first electrode being bonded to the back surface electrode;

a second principal surface on which a second electrode is disposed, and a first side surface;

a second circuit board including:

a third principal surface on which a third electrode is disposed, the third electrode being bonded to the second electrode; and a second side surface;

an electronic component housed in a recess, at least one of the second principal surface or the third principal surface including the recess; and a tube bonded to each of the first land and the second land to seal the recess in an airtight manner.

9. The image pickup unit according to claim 2, wherein the first and the second circuit boards are each formed of ceramic and the tube is formed of metal.

10. The image pickup unit according to claim 3, wherein the first land is distal to the recess and the second land is proximal to the recess.

11. The image pickup unit according to claim 3, wherein the first and the second side surfaces each extend in a longitudinal direction and the first and the second lands have a width in the longitudinal direction less than a width of the first and the second side surfaces in the longitudinal direction.

12. The image pickup unit according to claim 1, wherein the second circuit board further comprising a plurality of cable connection electrodes.

13. The image pickup unit according to claim 1, wherein the electronic component is a first electronic component, the image pickup unit further comprising one or more second electronic components for processing an image signal from the image sensor, the one or more second electronic components being disposed in the recess.

14. The image pickup unit according to claim 13, wherein the recess comprising first and second recess portions, the first recess portion being larger than the second recess portion, the first electronic component being disposed in the first recess portion, the one or more second electronic components being disposed in the second recess portion.

15. The image pickup unit according to claim 14, wherein the second recess portion is closer to the image sensor than the first recess portion.

16. The image pickup unit according to claim 1, wherein a portion of the recess is disposed on each of the second and the third principal surfaces.

17. The image pickup unit according to claim 3, wherein the first side surface comprises four first side surfaces;

the second side surface comprises four second side surfaces;

the first land is disposed on at least one of the four first side surfaces;

the second land is disposed on at least one of the four second side surfaces; and the tube is a rectangular tube having a rectangular shape in a cross-section orthogonal to a longitudinal axis direction.

18. The image pickup unit according to claim 17, wherein the recess is in communication with a gap between the second and the third principal surfaces; and the rectangular tube is configured to cover the gap and at least a portion of each of the four first and the four second side surfaces.

19. The image pickup unit according to claim 18, the rectangular tube extends in the longitudinal axis direction to cover at least the portion of each of the four first and the four second side surfaces such that the rectangular tube is bonded to each of the first and the second lands.

20. The image pickup unit according to claim 19, wherein each of the first and the second lands are disposed around the four first and the four second side surfaces, respectively, without a discontinuity.

* * * * *